US006248749B1

(12) United States Patent
Demarchez et al.

(10) Patent No.: US 6,248,749 B1
(45) Date of Patent: *Jun. 19, 2001

(54) USE OF INHIBITORS OF THE ACTIVITY OF RETINOIC ACID FOR TREATING SENSITIVE SKIN AND/OR ACUTE DAMAGE INDUCED BY UV RADIATION

(75) Inventors: Michel Demarchez, Le Bar sur Loup; André Jomard, Saint Vallier de Thiey, both of (FR)

(73) Assignee: Centre International de Recherches Dermatologiques Galderma, Valbonne (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/091,981
(22) PCT Filed: Oct. 20, 1997
(86) PCT No.: PCT/FR97/01879
  § 371 Date: Sep. 4, 1998
  § 102(e) Date: Sep. 4, 1998
(87) PCT Pub. No.: WO98/17925
  PCT Pub. Date: Apr. 30, 1998

(30) Foreign Application Priority Data

Oct. 31, 1996 (FR) .................................................. 96/13362

(51) Int. Cl.⁷ .......................... A31K 31/44; A31K 31/185
(52) U.S. Cl. ............................................ 514/278; 514/577
(58) Field of Search ....................... 549/23, 16; 546/153; 562/490; 424/44, 401; 435/7.1; 514/292, 291, 411, 553, 577

(56) References Cited

U.S. PATENT DOCUMENTS

| | | | | |
|---|---|---|---|---|
| 5,212,303 | * | 5/1993 | Shroot et al. | 544/69 |
| 5,364,617 | * | 11/1994 | Bush et al. | 424/59 |
| 5,391,766 | * | 2/1995 | Klaus et al. | 549/23 |
| 5,428,052 | * | 6/1995 | Shroot et al. | 514/415 |
| 5,434,180 | * | 7/1995 | Shroot et al. | 514/438 |
| 5,574,036 | * | 11/1996 | Bernardon et al. | 514/239.2 |
| 5,703,122 | * | 12/1997 | Duffy | 514/474 |
| 5,728,846 | * | 3/1998 | Vuligonda et al. | 549/16 |
| 5,770,383 | * | 6/1998 | Hwang et al. | 435/7.1 |
| 5,780,676 | * | 7/1998 | Boehm et al. | 562/490 |
| 5,786,379 | * | 7/1998 | Bernardon | 514/448 |
| 5,798,354 | * | 8/1998 | Bernardon et al. | 514/239.2 |
| 5,804,203 | * | 9/1998 | Hahn | 424/401 |
| 5,807,900 | * | 9/1998 | Bryce et al. | 514/725 |
| 5,827,500 | * | 10/1998 | Demarchez et al. | 424/9.1 |
| 5,952,382 | * | 9/1999 | Bernardon | 514/569 |

FOREIGN PATENT DOCUMENTS

| | | | |
|---|---|---|---|
| 679628 | * | 11/1995 | (EP) . |
| 0 740 937 | | 11/1996 | (EP) . |
| 96 30009 | | 10/1996 | (WO) . |

* cited by examiner

*Primary Examiner*—William R. A. Jarvis
*Assistant Examiner*—Vickie Kim
(74) *Attorney, Agent, or Firm*—Burns, Doane, Swecker & Mathis, L.L.P.

(57) ABSTRACT

The invention concerns tye use of a inhibitor of retinoic acid as sole ingredient in a pharmaceutical or cosmetic composition comprising administering effective amount of the composition to treat sensitive skin or skin damage induced by UV radiation.

7 Claims, No Drawings

USE OF INHIBITORS OF THE ACTIVITY OF RETINOIC ACID FOR TREATING SENSITIVE SKIN AND/OR ACUTE DAMAGE INDUCED BY UV RADIATION

This application of 371 of PCT/FR97/01879 filed on Oct. 20, 1997.

The present invention relates to a use of at least one inhibitor of the activity of retinoid acid in a cosmetic composition or for the manufacture of a pharmaceutical composition, the inhibitor of the activity of retinoid acid or the pharmaceutical composition being intended for treating sensitive skins and/or the acute damage induced by UV radiation.

It is known that some skins are more sensitive than others.

The symptoms of sensitive skins have until now been poorly characterized and the problem of these skins have been poorly defined because of this; no-one knew exactly the process implicated in the sensitivity of the skin. Some thought that a sensitive skin was a skin which reacted to cosmetic products, others that it was a skin which reacted to several external factors, not necessarily linked to cosmetic products.

Some tests have been evaluated in order to try to understand sensitive skins, for example tests based on lactic acid and DMSO which are known to be irritant substances: see for example the article by K. Lammintausta et al., Dermatoses, 1988, 36, pages 45–49; and the article by T. Agner and J. Serup, Clinical and Experimental Dermatology, 1989, 14, pages 214–217. However, these tests do not make it possible to characterize sensitive skins.

Moreover, sensitive skins have been assimilated with allergic skins.

Because the characteristics of sensitive skins were poorly known, it has up until now been very difficult to treat them, and they have been treated indirectly, for example by limiting, in cosmetic or dermatological compositions, the use of products with an irritant character such as surfactants, preservatives, solvents, propellants or perfumes.

Numerous clinical tests have since been performed and the symptoms linked to sensitive skins have thus been determined. These symptoms are in particular subjective signs, which are essentially dysaesthetic sensations. Dysaesthetic sensations are understood to mean sensations which are painful to a greater or lesser degree and which are felt in a cutaneous zone such as pricking, formication, itching or pruritus, inflammation, discomfort, twitching and the like.

It has been possible to show, in addition, that a sensitive skin was not an allergic skin. Indeed, an allergic skin is a skin which reacts to an external agent, an allergen, which triggers an allergic reaction. It is an immunological process which occurs only when an allergen is present and which affects only sensitized subjects. The essential characteristic of the sensitive skin is, according to the applicant, on the contrary, a mechanism of response to external factors, which can affect any individual, even though the individuals said to have sensitive skin react thereto more quickly than others. This mechanism is not immunological, it is aspecific.

Sensitive skins can be divided into two large clinical forms, the irritable and/or reactive skins and the intolerant skins.

An irritable and/or reactive skin is a skin which reacts through a pruritus, that is to say through itching, or through pricking, to various factors such as the environment (exposure to excessive UV rays), emotions, food, wind, rubbing, razors, soap, surfactants, hard water with a high chalk concentration, temperature variations or wool.

An intolerant skin is a skin which reacts to sensations of inflammation, twitching, formication and/or reddening, to various factors such as the environment (exposure to excessive UV rays), emotion and food.

Excessive exposure of the skin to UV rays can lead to acute cutaneous damage, such as an erythematous and/or irritated and/or red and/or swollen and/or oedematous and/or desquamatory skin. This acute cutaneous damage leads to what is commonly called "sunburn". This acute damage is to be distinguished from chronic damage, such as cancerous pathologies or a photoaged skin, which corresponds mainly to dermal damage, and subsidiarily to epidermal damage. "Sensitive" scalps have a more univocal clinical semiology: the sensations of pruritus and/or pricking and/or inflammation are essentially triggered by local factors such as rubbing, soap, surfactants, hard water with a high chalk concentration, shampoos or lotions. These sensations are also sometimes triggered by factors such as the environment, emotion and/or food.

Moreover, in some anatomical regions such as the large folds (inguinal, genital, axillary, popliteal, anal, submammary or elbow bend regions) and the feet, sensitive skin is manifested by pruriginous sensations and/or dysaesthetic sensations (inflammation, pricking) linked in particular to sweating, rubbing, wool, surfactants, hard water with a high chalk concentration and/or variations in temperature.

The products having an irritant character can be used in cosmetic or pharmaceutical compositions, and more particularly dermatological compositions, quite obviously for other effects. Thus, they are generally used as active agents, surfactants, preservatives, perfumes, solvents or propellants for the said compositions.

However, because of this undesirable effect, these products are generally used in very low doses. The use of these products in a small quantity may then prove to be of little advantage compared with the use of other less active but less irritant or not irritant products which are therefore used in a larger quantity.

Consequently, there is a need in the cosmetic and pharmaceutical field to find a means which makes it possible to use these products, without the latter exhibiting an irritant character which can be criticized by the user.

It is known, in general, that all-trans- retinoic acid acts on the differentiation and/or the proliferation of cells by interacting with nuclear receptors or RARs (retinoic acid receptors) contained in the cell nucleus. Numerous synthetic structural analogues of all-trans-retinoic acid or of 9-cis-retinoic acid, commonly called "retinoids", have been described so far in the literature. There are so far three identified sub-types of RAR receptors called α-RAR, β-RAR and γ-RAR, respectively. These receptors, after binding of the ligand (i.e. of all-trans-retinoic acid), interact with the promoter region of genes regulated by retinoic acid at the level of specific response elements (RARE).

Some analogues can bind and activate a particular RAR (α, β or γ) receptor sub-type. Finally, other analogues exhibit no particular selective activity towards these various receptors. To this end, and for example, all-trans-retinoic acid activates the RARs (RAR specific agonist ligand), all sub-types taken into consideration.

Retinoic acid and retinoids in general have been claimed for treating the following disorders or conditions: acne vulgaris, comedo-type acne, polymorphic acne, acne rosacea, nodulocystic acne, acne conglobata, senile acne, secondary acne such as solar acne, acne medicamentosa or occupational acne; other keratinization types of disorders, in particular ichthyosis, ichthyosiform states, Darrier's disease, keratosis palmaris et plantaris, leucoplakia and leucoplakia-like states, skin or mucosal (buccal) lichen; other dermatological conditions linked to a keratinization disorder with an inflammatory and/or immunoallergic component and in particular all forms of psoriasis whether cutaneous, mucosal or ungual, and even psoriatic rheumatism, or alternatively skin atopy, such as eczema or respiratory atopy or alternatively gingival hypertrophy; damage induced by UV radiation; skin ageing, whether photoinduced or chronologic or actinic keratoses and pigmentations or any pathology associated with chronologic or actinic ageing; healing disorders or vibices; disorders of sebaceous function such as hyperseborrhoea of acne or simple seborrhoea.

The combination of compounds which are agonists of the $\alpha$-RARs and $\gamma$-RARs with $\alpha$-RAR antagonists for treating photoaged skins has also been described in patent application WO 96/30009, specifying that the $\alpha$-RAR antagonists alone are not active for this type of treatment.

Retinoic acid and retinoids in general, by binding with the RAR receptors, make it possible to regulate the activity of the RAR receptors and to treat the above disorders or conditions.

As regards cutaneous atopies, it is known that they exhibit an immunological component.

Thus, it could therefore be thought that inhibitors of the activity of retinoic acid did not exhibit any activity on sensitive skin, as defined above, and on the damage induced by UV radiation.

It is known that retinoic acid and its analogues (also called retinoids) are capable of inducing the differentiation of mouse embryonic teratocarcinoma cells (F9). The secretion of plasminogen activator which accompanies this differentiation is an indication of the biological response of the F9 cells to the retinoids. It is also known that the capacity of these retinoids to induce plasminogen activator is directly correlated with the affinity which they have on the RAR receptors which are endogenous to the F9 cells (Skin pharmacol. 1990, 3, pp. 256–267).

The antagonists of retinoic acid inhibit the activity of retinoic acid or its metabolites at the cellular level. These are more particularly the RAR antagonists which bind to the RAR receptors, but do not induce the activity observed for retinoic acid or the retinoids, such as that observed on the F9 cells.

Thus, it has been shown that antagonists of the $\alpha$-RAR receptors inhibit the cellular differentiation induced by the retinoids on cells of the HL60 cell line or, on the contrary, reverse the inhibition of the proliferation of mouse B cells which is induced by the retinoids (C. Apfel & al., Proc. Natl. Acad. Sci. USA, 89, 1992, 7129–7133).

One of the aims of the present invention is therefore to provide compounds which can treat sensitive skins.

Another aim is to provide compounds which can in particular make it possible to use products in cosmetic or pharmaceutical compositions, more particularly dermatological compositions, without these products exhibiting an irritant character which can be criticized by the user.

Another aim is to provide a treatment of the acute cutaneous damage due to exposure to UV radiation.

These aims and others are achieved by the present invention which relates to the use of at least one inhibitor of the activity of retinoic acid in a cosmetic composition or for the preparation of a pharmaceutical composition, the inhibitor of the activity of retinoic acid or the pharmaceutical composition being intended for treating sensitive skins and/or the acute cutaneous damage induced by UV radiation.

The pharmaceutical composition is preferably a dermatological composition.

Sensitive skins and/or the acute cutaneous damage induced by UV radiation are as defined above.

Within the framework of the present invention, the treatment can be carried out in a preventive or curative manner. In the case of acute cutaneous damage induced by UV radiation, it is preferably carried out in a curative manner.

The present invention also relates to the use of at least one inhibitor of the activity of retinoic acid in a cosmetic composition or for the preparation of a pharmaceutical composition, the inhibitor of the activity of retinoic acid or the pharmaceutical composition being intended for treating cutaneous irritation and/or erythema and/or reddening and/or dysaesthetic sensations and/or sensations of inflammation and/or pruritus and/or pricking and/or formication and/or itching and/or twitching of the skin.

More particularly, the inhibitor of the activity of retinoic acid or the pharmaceutical composition is intended for treating erythema and/or irritation and/or reddening and/or swelling and/or oedema and/or desquamation due to UV radiation.

The inhibitors of the activity of retinoic acid can act according to two pathways, the first by accelerating the cellular metabolism of retinoic acid so as to reduce the cellular concentration of the latter, the second by antagonizing its action at the cellular level.

The inhibitors of the activity of retinoic acid can therefore be, according to the invention, accelerators of the metabolism of retinoic acid or antagonists, reverse agonists or partial agonists of retinoic acid.

By antagonists of retinoic acid, there is preferably understood according to the invention the compounds which inhibit the action of retinoic acid and/or of its metabolites and/or of the retinoids. They are more particularly RAR antagonists which bind to the RAR receptors without, however, activating them. Thus, they do not induce the differentiation of these F9 cells, but bind nevertheless to the RARs, this binding being of the antagonist type. The F9 test is that described in the article of Skin pharmacol. 1990, 3, pp. 256–267.

The ability of a compound to bind to the RARs is determined by means of tests which are conventional for persons skilled in the art. These tests are in particular described in the following references: (1) "Selective Synthetic Ligands for Nuclear Retinoic Acid Receptor Subtypes" in RETINOIDS, Progress in Research and Clinical Applications, Chapter 19 (pp 261–267), Marcel Dekker Inc, edited by Maria A. Livrea and Lester Packer; (2) "Synthetic Retinoids: Receptor Selectivity and Biological Activity" in Pharmacol Skin, Basel, Karger, 1993, Volume 5, pp 117–127; (3) "Selective Synthetic Ligands for Human Nuclear Retinoic Acid Receptors" in Skin Pharmacology, 1992, Vol. 5, pp 57–65; (4) "Identification of Synthetic Retinoids with Selectivity for Human Nuclear Retinoic Acid Receptor-$\gamma$" in Biochemical and Biophysical Research Communications, Vol. 186, No. 2, July 1992, pp 977–983; (5) "Selective High Affinity RAR-$\alpha$ or RAR-$\beta$ Retinoic Acid Receptor Ligands" in Mol. Pharmacol., Vol. 40, pp 556–562.

The antagonists of retinoic acid are in particular the compounds described in patent applications EP 661 259, EP 658 553, EP 568 898, WO 95/33745 and WO 94/14777, and in several scientific publications, in particular EYROLLES & al (J. Med. Chem., 37, 1994, 1508–1517; Med. Chem. Res., 2, 1992, 361–367) and KANEKO & al (Med. Chem. Res., 1, 1991, 220–225) incorporated herein by reference and which inhibit the action of retinoic acid and/or of the retinoids.

The RAR antagonists of use according to the invention are in particular selected from the following compounds:

4-[7-(1-adamantyl)-6-methoxyethoxymethoxy-2-naphthyl] benzoic acid,

4-[7-(1-adamantyl)-6-methoxyethoxymethoxy-2-naphthyl] salicylic acid,

4-{f[5,6-dihydro-5,5-dimethyl-8-(4-methylphenyl)-2-naphthalenyl]ethynyl}benzoic acid, (E)-4-[2-(4,4-dimethyl-7-heptyloxy-1,1-dioxo-3,4-dihydro-2H-1-benzothiopyran-6-yl)propenyl]benzoic acid, 4-[4,5,7,8,9,10-hexahydro-7,7,10,10-tetramethyl-1-(3-pyridylmethyl)anthra[1,2-b]pyrrol-3-yl]benzoic acid, 4-[4,5,7,8,9,10-hexahydro-7,7,10,10-tetramethyl-1-(3-pyridylmethyl)thioanthra[1,2-b]pyrrol-3-yl]benzoic acid, 4-[4,5,7,8,9,10-hexahydro-7,7,10,10-tetramethyl-1-(3-pyridylmethyl)anthra[1,2-d]pyrazol-3-yl]benzoic acid, 4-[3-(diamantyl)-4-methoxybenzamido]benzoic acid, 4-[3-(diamantyl)-4-methoxybenzoyloxy]benzoic acid, 4-(N-phenyl-5,6,7,8-tetrahydro-5,5,8,8-tetramethylnaphtho[2,3-d]imidazol-2-yl)benzoic acid, 4-(N-benzyl-5,6,7,8-tetrahydro-5,5,8,8-tetramethylnaphtho[2,3-d]imidazol-2-yl)benzoic acid, 4-(5H-7,8,9,10-tetrahydro-5,7,7,10,10-pentamethylbenzo[c]-naphtho[2,3-b][1,4]diazepin-3-yl)benzoic acid, 4-[1-(1-methoxy-2,2,2-trifluoroethyl)-5,6,7,8-tetrahydro-5,5,8,8-tetramethyl-3-anthracenyl]benzoic acid, 7-[3-(1-adamantyl)-4-methoxyphenyl]-3,7-dimethyl-2,4,6-heptatrienoic acid, 6-[7-(1-adamantyl)-6-methoxyethoxymethoxy-2-naphthyl] nicotinic acid, 4-(5,5-dimethyl-8-phenyl-5,6-dihydronaphthalen-2-ylethynyl)benzoic acid, 4-(5,5-dimethyl-8-p-tolyl-5,6-dihydronaphthalen-2-ylethynyl)benzoic acid.

Preferably, 4-[7-(1-adamantyl)-6-methoxyethoxymethoxy-2-naphthyl]benzoic acid, 4-[7-(1-adamantyl)-6-methoxyethoxymethoxy-2-naphthyl]salicylic acid, 7-[3-(1-adamantyl)-4-methoxyphenyl]-3,7-dimethyl-2,4,6-heptatrienoic acid or 6-[7-(1-adamantyl)-6-methoxyethoxymethoxy-2-naphthyl]nicotinic acid is used.

The cosmetic or pharmaceutical composition comprising at least one inhibitor of the activity of retinoic acid comprises a cosmetically or pharmaceutically acceptable carrier compatible with the mode of administration selected.

The quantity of inhibitor of the activity of retinoic acid is an effective quantity depending of course on the desired treatment and the nature of the chosen compound; it is therefore determined by persons skilled in the art.

The administration of the compounds according to the invention may be carried out by the systemic (especially enteral or parenteral), topical or ocular route.

By the enteral route, the composition is more particularly a pharmaceutical composition which may be provided in the form of tablets, gelatine capsules, sugar-coated tablets, syrups, suspensions, solutions, powders, granules, emulsions, lipid or polymeric microspheres or nanospheres or vesicles which allow a controlled release. By the parenteral route, the composition, more particularly the pharmaceutical composition, may be provided in the form of solutions, emulsions or suspensions for infusion or for injection.

The inhibitors of the activity of retinoic acid, more particularly the antagonists of retinoic acid are generally administered by the systemic route in a daily dose of about 0.01 mg/kg to 100 mg/kg of body weight, and this at the rate of 1 to 3 doses.

By the topical route, the composition is a cosmetic or pharmaceutical composition, more particularly intended for the treatment of the skin. It can therefore be provided in the form of solutions or suspensions, ointments, pommades, creams, milks, gels, powders, impregnated pads, lotions, sprays, or foaming or cleansing products. It can also be provided in the form of lipid or polymeric microspheres or nanospheres or vesicles or of polymeric patches, hydrogels or dressings allowing a controlled release. This composition for the topical route can, moreover, be provided either in anhydrous form or in an aqueous form.

It can also be used on hair, to treat the scalp, in the form of aqueous, alcoholic or aqueous- alcoholic solutions, in the form of creams, gels, emulsions, foams or alternatively in the form of aerosol compositions also containing a pressurized propelling agent.

These compositions constitute in particular cleansing, protective, treatment or care creams for the face, the hands, the feet, the large anatomical folds or the body (for example day creams, night creams, make-up removing creams, foundation creams, anti-sun creams), fluid foundations, make-up removing milks, protective or care body milks, anti-sun milks, lotions, gels or foams for skin care, such as cleansing lotions, anti-sun lotions, artificial tanning lotions, bath compositions, deodorant compositions containing a bactericidal agent, aftershave gels or lotions, depilatory creams, compositions against insect bites, anti-pain compositions.

The compositions according to the invention may also consists of solid preparations constituting cleansing cakes or soaps.

The compositions may also be packaged in the form of an aerosol composition also containing a pressurized propelling agent.

The inhibitor of the activity of retinoic acid may also be incorporated into various compositions for hair care, and particularly shampoos, hair setting lotions, treatment lotions, hair-styling creams or gels, dye compositions (particularly oxidation dyes) optionally in the form of dyeing shampoos, restructuring lotions for the hair, permanent waving compositions (particularly compositions for the first stage of a permanent waving), anti-hair loss lotions or gels and the like.

By the ocular route, the composition may in this case be provided in the form of ointments, creams, gels or collyria which are appropriate for this specific application.

This composition for topical or ocular use contains at least one antagonist of retinoic acid at a concentration preferably ranging from 0.000001% to 5% by weight relative to the total weight of the composition, more particularly ranging from 0.0001% to 0.1% by weight.

The composition according to the invention may, in addition, contain inert or even pharmacodynamically or cosmetically active additives or combinations of these additives, and in particular wetting agents; emollients; moisturizing agents such as glycerol, PEG 400, thiamorpholinone and its derivatives or alternatively urea; carotenoids and, in particular, β-carotene.

The composition may also contain taste-enhancing agents, preservatives such as esters of parahydroxybenzoic acid, stabilizing agents, humidity-regulating agents, pH-regulating agents, osmotic pressure-modifying agents, emulsifying agents, photoprotective agents such as UV-A and/or UV-B screening agents, hydrophilic or lipophilic anti-oxidants, such as α-tocopherol, butylated hydroxyanisole or butylated hydroxytoluene, chelators such as EDTA and its salts.

The inhibitor of the activity of retinoic acid and the other active compounds can be administered together in the same cosmetic or pharmaceutical composition, or alternatively separately in separate compositions, simultaneously or spaced out over time.

The quantities of the various constituents of the compositions according to the invention are those conventionally used in the fields considered.

Of course the nature and the quantity of these constituents are chosen so as not to interfere with the activity of the inhibitor of the activity of retinoic acid for treating sensitive skins and/or the acute cutaneous damage induced by UV radiation.

The inhibitors of the activity of retinoic acid can be combined, inter alia, with active agents intended in particular for the prevention and/or treatment of skin conditions.

Among these active agents, there may be mentioned, by way of example:

agents modulating skin differentiation and/or proliferation and/or pigmentation such as vitamin D and its derivatives, oestrogens such as estradiol, kojic acid or hydroquinone;

antibacterials such as clindamycin phosphate, erythromycin or antibiotics of the tetracycline class;

antiparasitic agents, in particular metronidazole, crotamiton or pyrethrinoids;

antifungal agents, in particular the compounds belonging to the imidazole class such as econazole, ketoconazole or miconazole or their salts, the polyene compounds, such as amphotericin B, the compounds of the allylamine family, such as terbinafine, or octopirox;

steroidal anti-inflammatory agents such as hydrocortisone, betamethasone valerate or clobetasol propionate, or non-steroidal anti-inflammatory agents such as ibuprofen and its salts, diclofenac and its salts, acetylsalicylic acid, acetaminophen or glycyrrhetinic acid;

anaesthetic agents such as lidocaine hydrochloride and its derivatives;

antipruriginous agents such as thenaldine, trimeprazine or cyproheptadine;

antiviral agents such as acyclovir;

keratolytic agents such as alpha- and beta- hydroxycarboxylic or beta-ketocarboxylic acids, their salts, amides or esters and more particularly hydroxy acids such as glycolic acid, lactic acid, salicylic acid, citric acid and, in general, fruit acids and 5-n-octanoylsalicylic acid;

anti-free radical agents, such as alpha-tocopherol or its esters, superoxide dismutases, certain metal chelators or ascorbic acid and its esters;

antiseborrhoeic agents such as progesterone;

antidandruff agents such as octopirox or zinc pyrithione;

anti-acne agents such as benzoyl peroxide.

Advantageously, the inhibitors of the activity of retinoic acid are combined with active agents with an irritant side effect which are commonly used in the cosmetic or dermatological field. The presence of an inhibitor in a cosmetic or dermatological composition containing an active agent having an irritant effect makes it possible to substantially attenuate, or even suppress this effect.

Accordingly, a further subject of the invention is a composition containing a cosmetically or pharmaceutically acceptable medium and at least one active agent with an irritant side effect, with the exception of retinoic acid and retinoids, characterized in that it comprises at least one inhibitor of the activity of retinoic acid.

In particular, the active agents with an irritant side effect are selected from $\alpha$-hydroxy acids, $\beta$-hydroxy acids, $\alpha$-keto acids, $\beta$-keto acids, anthralins, anthranoids, peroxides, minoxidil, lithium salts, antimetabolites, vitamin D and its derivatives.

Because of its importance in the sun domain, another subject of the present invention is a composition containing a cosmetically or pharmaceutically acceptable medium and at least one photoprotective agent, characterized in that it comprises at least one inhibitor of the activity of retinoic acid.

By way of photoprotective agent, there may be used organic screening agents which are hydrophlic or lipophilic conventional sun-screening agents active in the UV-A and/or UV-B region. By way of examples, these screening agents may be chosen, alone or as a mixture, from 2-phenylbenzimidazole-5-sulphonic acid and its salts, cinnamic derivatives, salicylic derivatives, benzylidenecamphor derivatives, triazine derivatives, benzophenone derivatives, dibenzoylmethane derivatives, $\beta,\beta$-diphenylacrylate derivatives, p-aminobenzoic acid derivatives, menthyl anthranilate, the screening polymers and screening silicones described in application WO-93-04665. Other examples of organic screening agents are given in patent application EP-A 0,487,404.

The organic screening agent(s) are generally present in the compositions according to the invention in an amount ranging from 0.1% to 30%, preferably from 0.5 to 15% by weight relative to the total weight of the composition.

A second category of photoprotective agents which are particularly suitable for the compositions according to the invention is that of pigments. Preferably, inorganic nanopigments (mean size of the primary particles: generally between 5 nm and 100 nm, preferably between 10 and 50 nm) of metallic oxides, coated or otherwise, are used such as for example nanopigments of titanium oxide (amorphous or crystallized in the form of rutile and/or anatase), of iron, of zinc, of zirconium or of cerium which are all photoprotective agents well known per se which act by physically blocking (reflection and/or diffusion) the UV radiation. Conventional coating agents are moreover alumina and/or aluminium stearate or alternatively silicones. Such nanopigments of metallic oxides, coated or non-coated, are in particular described in patent applications EP-A-0,518,772 and EP-A-0,518,773.

The inorganic (nano)pigment(s) may be present in the compositions according to the invention in an amount of between 0.1% and 30%, preferably from 0.5% to 10% by weight relative to the total weight of the composition.

The subject of the present invention is, in addition, a process of cosmetic treatment, characterized in that a composition as described above, containing at least one inhibitor of the activity of retinoic acid in a cosmetically acceptable medium is applied to the skin and/or the hair.

The process of cosmetic treatment of the invention may be carried out in particular by applying the hygiene or cosmetic compositions as defined above, according to the usual technique for using these compositions. For example: application of creams, gels, sera, lotions, make-up removing milks or anti-sun compositions to the skin or to dry hair, application of a hair lotion to wet hair, or shampoos.

Several examples will now be given by way of illustration and with no limitation being implied.

EXAMPLE 1

Study of the activity of the inhibitors of the activity of retinoic acid for protecting the skin against the deleterious biological effects induced by UV radiation.

The aim of this example is to demonstrate the activity of an RAR antagonist in protecting the skin against the acute biological cutaneous effects induced by UVB radiation.

Method

For these studies, a UVB tube having a peak at 315 nm is.used.

A single irradiation at the dose of 120 mJ/cm$^2$ is applied to the ear in Balb/c mice. The irradiation is applied under anaesthetic, the animals, outside the irradiated zone, being protected by a screen.

4-[7-(1-Adamantyl)-6-methoxyethoxymethoxy-2-naphthyl] benzoic acid (RAR antagonist) in solution in acetone at the concentrations of 0.01%, 0.03% and 0.1%, or the vehicle alone, is administered by topical application to the irradiated ear, in a volume of 20 microliters.

The treatment is administered 30 minutes, 24 hours, 48 hours and 72 hours after irradiation.

Every day for 11 days after irradiation (from D1 to D11), clinical observations are carried out and the oedema is quantified by measuring the thickness of the ear with the aid of a micrometer.

Results

In the animals irradiated and not treated, or treated with the vehicle alone, an erythema is observed and an oedema which is clinically visible 24 hours after irradiation and reaching a maximum value 9 days after irradiation. Desquamation appears 4 days after irradiation. This phenomenon becomes accentuated during the second week after irradiation.

In the animals treated with 4-[7-(1-adamantyl)-6-methoxyethoxymethoxy-2-naphthyl]benzoic acid, a dose-dependent reduction in the erythema, the oedema and the desquamation is observed. The value of the area under the curve of the thickness of the ear determined by the trapezium method over the D1–D11 period is reduced in a statistically significant manner by the treatment at the doses of 0.03% and 0.1%, by 26% and 55% respectively.

These results clearly show that the inhibitors of the activity of retinoic acid or of its metabolites and more particularly the RAR antagonists, exhibit a reparatory activity on the acute deleterious biological effects induced by UVB radiation.

EXAMPLE 2

Study of the evaluation of the inhibitors of retinoic acid for protecting the skin against the acute deleterious effects induced by UV radiation.

This example is intended to demonstrate the activity of an RAR antagonist in protecting the skin against the acute cutaneous biological effects induced by UVB radiation.

Method

Human skin obtained from a healthy donor is transplanted in nude mice according to the method described by Demarchez & al (M. Demarchez & al, Develop. Biology, 113, 1986, 90–96; M. Demarchez & al, Develop. Biology, 121, 1987, 119–129).

Five months after the transplantation, a single irradiation at the dose of 300 mJ/cm$^2$ is applied to half of the transplant with the aid of a UVB lamp having a peak at 315 nanometres. The other half of the transplant protected by a screen during the irradiation is used as an intra-individual control.

4-[7-(1-Adamantyl)-6-methoxyethoxymethoxy-2-naphthyl]-benzoic acid (RAR antagonist) in solution in acetone at the concentration of 0.1%, or the vehicle alone, is administered by topical application to the transplant on the day of irradiation and then once per day during the four days following the irradiation.

24 hours after the last treatment, the mice are subjected to euthanasia and the skin of the transplants is removed and fixed by freezing for an immunohistochemical study. Various antibodies are used to study the effect of UVB and of the treatments on the cutaneous morphology: anti-human involucrin (study of epidermal differentiation), AE1 (anti-keratin monoclonal antibody), anti-HLADr (Langerhans' cells).

Results UVB radiation induces, in the epidermis of the transplants treated with the vehicle alone, a slight hyperplasia, a hypergranulosis, a parakeratosis, a disruption of the epidermal differentiation and of the "sun burn cells".

The treatment with 4-[7-(1-adamantyl)-6-methoxyethoxymethoxy-2-naphthyl]benzoic acid limits the hypergranulosis and the hyperkeratosis, and reduces the number of "sun burn cells".

These results clearly show that the inhibitors of the activity of retinoic acid or of its metabolites, and more particularly the RAR antagonists, exhibit a reparatory activity on the acute deleterious biological effects induced by UVB radiation.

EXAMPLE 3

Study of the evaluation of the inhibitors of retinoic acid as treatment for sensitive skins.

This example is intended to demonstrate the activity of an RAR antagonist as regulator of cutaneous homeostasis in the border zones of a transplant.

Method Human skin obtained from a healthy donor is transplanted in nude mice according to the method described by Demarchez & al (M. Demarchez & al, Develop. Biology, 113, 1986, 90–96; M. Demarchez & al, Develop. Biology, 121, 1987, 119–129). It is well established that in this model of human skin transplanted in nude mice, the periphery of the transplants is a zone which is particularly sensitive to chemical agents such as irritant products or to physical agents such as UV. Thus, this peripheral zone may be considered as a model of sensitive skin.

Three months after transplantation, 4-[7-(1-adamantyl)-6-methoxyethoxymethoxy-2-naphthyl]benzoic acid (RAR antagonist), in solution in acetone at the concentration of 0.1%, or the vehicle alone, is administered by topical application to the transplant once per day for six weeks. 24 hours after the last treatment, the mice are subjected to euthanasia and the skin of the transplants is removed and fixed by freezing for an immunohistochemical study. Various antibodies are used to study the effect of UVB and of the treatments on the cutaneous morphology: anti-human involucrin (study of epidermal differentiation), AE1 (anti-keratin monoclonal antibody).

Results

The transplants treated with the vehicle alone exhibit disruption in epidermal differentiation in the transplant border zone.

4-[7-(1-Adamantyl)-6-methoxyethoxymethoxy-2-naphthyl]benzoic acid does not modify the histological appearance of the transplants except at the level of the borders of transplants where it regulates epidermal differentiation.

These results clearly show that the inhibitors of the activity of retinoic acid or of its metabolites, and more particularly the RAR antagonists, exhibit a modulatory activity on cutaneous homeostasis in sensitive skins.

EXAMPLE 4

Study of the evaluation of the inhibitors of retinoic acid as a treatment for sensitive skins.

This example is intended to demonstrate the activity of an RAR antagonist as a regulator of cutaneous homeostasis in transplant border zones.

Method

Human skin obtained from a healthy donor is transplanted in nude mice according to the method described by Demarchez & al (M. Demarchez & al, Develop. Biology, 113, 1986, 90–96; M. Demarchez & al, Develop. Biology, 121, 1987, 119–129). It is well established that in this model of human skin transplanted in nude mice, the periphery of the transplants is a zone which is particularly sensitive to chemical agents such as irritant products or to physical agents such as UV. Thus, this peripheral zone may be considered as a model of sensitive skin.

Five months after transplantation, 4-[7-(1-adamantyl)-6-methoxyethoxymethoxy-2-naphthyl]benzoic acid (RAR antagonist) or 4-[7-(1-adamantyl)-6-methoxyethoxymethoxy-2-naphthyl]salicylic acid in suspension in cremophor EL 25%, or the vehicle alone, is administered orally once per day for 7 days. 24 hours after the last treatment, the mice are subjected to euthanasia and the skin of the transplants is removed and fixed by freezing for an immunohistochemical study. Various antibodies are used to study the effect of the treatments on the cutaneous morphology: anti-human involucrin (study of epidermal differentiation), AE1 (anti-keratin monoclonal antibody)

Results

The transplants treated with the vehicle alone exhibit disruption of epidermal differentiation in the transplant border zone.

4-[7-(1-Adamantyl)-6-methoxyethoxymethoxy-2-naphthyl]-benzoic acid and 4-[7-(1-adamantyl)-6-methoxyethoxymethoxy- 2-naphthyl]salicylic acid do not modify the histological appearance of the transplants except at the level of the borders of transplants where it regulates epidermal differentiation.

These results clearly show that the inhibitors of the activity of retinoic acid or of its metabolites, and more particularly the RAR antagonists, exhibit a modulatory activity on cutaneous homeostasis in sensitive skins.

EXAMPLE 5

The compositions below are examples of compositions capable of being used to apply or administer antagonists of retinoic acid with the aim of treating sensitive skins and/or the acute damage due to UV radiation.

A - ORAL ROUTE (a) Immediate-release 0.2 g tablet (granulation)

| | |
|---|---|
| Antagonist of retinoic acid | 0.0010 g |
| Lactose codex | 0.1204 g |
| Microcrystalline cellulose (Avicel PH 101) | 0.0640 g |
| Polyvinylpyrrolidone (Kollidon K30) | 0.0060 g |
| Colloidal silica (Aerosil 200) | 0.0006 g |
| Magnesium stearate | 0.0020 g |
| Sodium starch glycolate (Explotab) | 0.0060 g |
| Purified water qs granulation | |

(b) Immediate-release 0.8 g tablet (direct compression)

| | |
|---|---|
| Antagonist of retinoic acid | 0.0800 g |
| Modified starch (Starch 1500) | 0.2984 g |
| Microcrystalline cellulose (Avicel PH 102) | 0.4000 g |
| Colloidal silica (Aerosil 200) | 0.0016 g |
| Magnesium stearate | 0.0040 g |
| Sodium Croscarmellose (Ac-Di-Sol) | 0.0160 g |

(c) 0.2 g gelatin capsule (soft capsule or hard gelatin capsule filled with liquid)

| | |
|---|---|
| Antagonist of retinoic acid | 0.0050 g |
| Unsaturated polyglycosylated glycerides or vegetable oil (soyabean, maize and the like) | 0.1845 g |
| White beeswax or hydrogenated castor oil | 0.0100 g |
| BHT | 0.0001 g |
| dl-α-tocopherol | 0.0004 g |

(d) Oral solution in 5 ml vials

| | | |
|---|---|---|
| Antagonist of retinoic acid | | 0.0001 g |
| Glycerol | | 0.7500 g |
| Sorbitol | | 1.0000 g |
| Propylene glycol | | 1.0000 g |
| Polyvinylpyrrolidone (Kollidon K25) | | 0.5000 g |
| Sodium cyclamate | | 0.0050 g |
| Sodium parahydroxybenzoate | | 0.0040 g |
| Flavouring | qs | |
| Purified water | qs | 5 ml |

B - TOPICAL ROUTE (a) Ointment

| | |
|---|---|
| Antagonist of retinoic acid | 0.020 g |
| Isopropyl myristate | 81.700 g |
| Fluid petroleum jelly | 9.100 g |
| Silica ("Aerosil 200" sold by Degussa) | 9.180 g |

(b) Ointment

| | | |
|---|---|---|
| Antagonist of retinoic acid | | 0.300 g |
| Petroleum jelly codex | qs | 100 g |

(c) Non-ionic water-in-oil cream

| | | |
|---|---|---|
| Antagonist of retinoic acid | | 0.100 g |
| Mixture of emulsifying lanolin alcohols, of waxes and of oils ("Eucerine anhydre" sold by BDF) | | 39.900 g |
| Methyl para-hydroxybenzoate | | 0.075 g |
| Propyl para-hydroxybenzoate | | 0.075 g |
| Sterile demineralized water | qs | 100 g |

(d) Lotion

| | |
|---|---|
| Antagonist of retinoic acid | 0.100 g |
| Polyethylene glycol (PEG 400) | 69.900 g |
| Ethanol 95% | 30.000 g |

(e) Non-ionic oil-in-water cream

| | | |
|---|---|---|
| Antagonist of retinoic acid | | 1.000 g |
| Cetyl alcohol | | 4.000 g |
| Glycerol monostearate | | 2.500 g |
| PEG 50 stearate | | 2.500 g |
| Shea butter | | 9.200 g |
| Propylene glycol | | 2.000 g |
| Methyl para-hydroxybenzoate | | 0.075 g |
| Propyl para-hydroxybenzoate | | 0.075 g |
| Sterile demineralized water | qs | 100 g |

What is claimed is:

1. A method for treating sensitive skin or acute cutaneous damage induced by UV radiation consisting essentially of applying an effective amount of a retinoid inhibitor as the sole active ingredient in a pharmaceutical or cosmetic composition.

2. The method of claim 1 characterized in that the refinoid inhibitor is chosen from the following compounds:
4-[7-(1-adamantyl)-6-methoxyethoxymethoxy-2-naphthyl]benzoic acid,
4-[7-(1-adamantyl)-6-methoxyethoxymethoxy-2-naphthyl]salicylic acid,
4-{[5,6-dihydro-5,5-dimethyl-8-(4-methylphenyl)-2-naphthalenyl]ethynyl}benzoic acid,
(E)-4-[2-(4,4-dimethyl-7-heptyloxy-1,1-dioxo-3,4-dihydro-2H-1-benzothiopyran-6-yl)propenyl]benzoic acid,
4-[4,5,7,8,9,10-hexahydro-7,7,10,10-tetramethyl-1-(3-pyridylmethyl)anthra[1,2-b]pyrrol-3-yl]benzoic acid,
4-[4,5,7,8,9,10-hexahydro-7,7,10,10-tetramethyl-1-(3-pyridylmethyl)thioanthra[1,2-b]pyrrol-3-yl]benzoic acid,
4-[4,5,7,8,9,10-hexahydro-7,7,10,10-tetramethyl-1-(3-pyridylmethyl)anthra[1,2-d]pyrazol-3-yl]benzoic acid,
4-[3-(diamantyl)-4-methoxybenzamido]benzoic acid,
4-[3-(diamantyl)-4-methoxybenzoyloxy]benzoic acid,
4-(N-phenyl-5,6,7,8-tetrahydro-5,5,8,8-tetramethylnaphtho[2,3-d]imidazol-2-yl)benzoic acid, 4-(N-benzyl-5,6,7,8-tetrahydro-5,5,8,8-tetramethylnaphtho[2,3-d]imidazol-2-yl)benzoic acid, 4-(5H-7,8,9,10-tetrahydro-5,7,7,10,10-pentamethylbenzo[c]-naphtho[2,3-b][1,4]diazepin-3-yl)benzoic acid, 4-[1-(1-methoxy-2,2,2-trifluoroethyl)-5,6,7,8-tetrahydro-5,5,8,8-tetramethyl-3-anthracenyl]benzoic acid, 7-[3-(1-adamantyl)-4-methoxyphenyl]-3,7-dimethyl-2,4,6-heptatrienoic acid, 6-[7-(1-adamantyl)-6-methoxyethoxymethoxy-2-naphthyl]nicotinic acid, 4-(5,5-dimethyl-8-phenyl-5,6-dihydronaphthalen-2-ylethynyl)benzoic acid, and 4-(5,5-dimethyl-8-p-tolyl-5,6-dihydronaphthalen-2-ylethynyl)benzoic acid.

3. The method of claim 2, characterized in that the retinoid inhibitor is chosen from:

4-[7-(1-adamantyl)-6-methoxyethoxymethoxy-2-naphthyl]benzoic acid,

4-[7-(1-adamantyl)-6-methoxyethoxymethoxy-2-naphthyl]salicylic acid,

7-[3-(1-adamantyl)-4-methoxyphenyl]-3,7-dimethyl-2,4,6-heptatrienoic acid, and

6-[7-(1-adamantyl)-6-methoxyethoxymethoxy-2-naphthyl]nicotinic acid.

4. A method for treating a condition selected from the group consisting of cutaneous irritation, erythema, reddening, dysaesthetic sensations, sensations of inflammation, pruritus, prickling, formication, itching, and twitching of the skin, consisting essentially of applying a cosmetic or pharmaceutical composition consisting essentially of an effective amount of at least one inhibitor of retinoic acid.

5. A method for treating at least one of erythema, irritation, reddening, swelling, edema, and/or desquamation attributable to UV radiation consisting essentially of applying an effective amount of a pharmaceutical composition consisting essentially of at least one inhibitor of retinoic acid.

6. The method of claim 1, wherein said pharmaceutical composition is a dermatological composition.

7. The method of claim 1, wherein said composition alleviates sensitive skin or acute cutaneous damage induced by UV radiation.

* * * * *

UNITED STATES PATENT AND TRADEMARK OFFICE
CERTIFICATE OF CORRECTION

PATENT NO. : 6,248,749 B1
DATED : June 19, 2001
INVENTOR(S) : Demarchez et al.

It is certified that error appears in the above-identified patent and that said Letters Patent is hereby corrected as shown below:

Title page,
ABSTRACT, please delete "tye" and insert -- the -- and please insert -- the activity of -- after the phrase "inhibitor of."

Column 9,
Line 37, please insert -- the activity of -- after the phrase "inhibitors of."

Column 10,
Lines 16 and 59, please insert -- the activity of -- after the phrase "inhibitors of."

Column 12,
Lines 46 and 49, please delete "retinoid" and insert -- retinoic acid activity. --

Column 13,
Line 16, please delete "retinoid" and insert -- retinoic acid activity. --

Column 14,
Lines 9 and 15, please insert -- the activity of -- after the phrase "inhibitor of."

Signed and Sealed this

Twenty-third Day of April, 2002

*Attest:*

*Attesting Officer*

JAMES E. ROGAN
*Director of the United States Patent and Trademark Office*